(12) United States Patent
Pollegioni et al.

(10) Patent No.: US 7,399,624 B2
(45) Date of Patent: Jul. 15, 2008

(54) CEPHALOSPORIN C ACYLASES

(75) Inventors: Loredano Pollegioni, Milan (IT); Mirella Pilone, Milan (IT); Gianluca Molla, Jerago Con Orago (IT); Eugenio Cucchetti, Cuggiono (IT); Roberto Verga, Agnadello (IT); Walter Cabri, Rozzano (IT)

(73) Assignee: Antibioticos S.p.A., Rodano (IT)

( * ) Notice: Subject to any disclaimer, the term of this patent is extended or adjusted under 35 U.S.C. 154(b) by 556 days.

(21) Appl. No.: 11/032,090

(22) Filed: Jan. 11, 2005

(65) Prior Publication Data

US 2005/0158818 A1 Jul. 21, 2005

(30) Foreign Application Priority Data

Jan. 12, 2004 (IT) .................. MI2004A0016

(51) Int. Cl.
*C12N 6/86* (2006.01)
*C12N 15/55* (2006.01)
*C12P 35/06* (2006.01)

(52) U.S. Cl. .................. 435/231; 435/47; 536/23.2
(58) Field of Classification Search .................. None
See application file for complete search history.

(56) References Cited

U.S. PATENT DOCUMENTS

| | | | |
|---|---|---|---|
| 5,192,678 A * | 3/1993 | Iwami et al. | 435/228 |
| 5,320,948 A * | 6/1994 | Iwami et al. | 435/47 |
| 5,336,613 A * | 8/1994 | Niwa et al. | 435/228 |
| 5,457,032 A * | 10/1995 | Quax et al. | 435/43 |
| 5,677,141 A * | 10/1997 | Isogai et al. | 435/47 |
| 5,695,978 A * | 12/1997 | Quax | 435/230 |
| 5,804,429 A * | 9/1998 | Niwa et al. | 435/228 |
| 5,891,703 A * | 4/1999 | Van Der Laan et al. | 435/230 |
| 5,919,648 A * | 7/1999 | Burr et al. | 435/47 |
| 6,303,302 B1 * | 10/2001 | Rupp et al. | 435/6 |
| 6,528,300 B2 * | 3/2003 | Binder et al. | 435/228 |
| 2005/0261270 A1 * | 11/2005 | Wong et al. | 514/210.02 |
| 2006/0292665 A1 * | 12/2006 | Sio et al. | 435/51 |

FOREIGN PATENT DOCUMENTS

| | | | |
|---|---|---|---|
| JP | 07-222587 | * | 8/1995 |
| JP | 08-098686 | * | 4/1996 |
| JP | 08-205864 | * | 8/1996 |
| WO | WO 2005/014821 | * | 2/2005 |

OTHER PUBLICATIONS

Itakura, K., et al., 1984, "Synthesis and use of synthetic oligonucleotides", Annual Review of Biochemistry, vol. 53, pp. 323-356.*

Aramori, I., et al., 1991, "Cloning and nucleotide sequencing of new glutaryl 7-ACA and cephalosporin C acylase genes from Pseudomonas strains", Journal of Fermentation and Bioengineering, vol. 72, No. 4, pp. 232-243.*

Ishii, Y., et al., 1995, "High-level production, chemical modification and site-directed mutagenesis of a cephalosporin C acylase from Pseudomonas strain N176", European Journal of Biochemistry, vol. 230, pp. 773-778.*

Otten, L., et al., 2002, "Altering the substrate specificity of cephalosporin C acylase by directed evolution of the β-subunit", The Journal of Biological Chemistry, vol. 277, No. 44, pp. 42121-42127.*

* cited by examiner

*Primary Examiner*—Nashaat T. Nashed
*Assistant Examiner*—William W. Moore
(74) *Attorney, Agent, or Firm*—Rothwell, Figg, Ernst & Manbeck, P.C.

(57) ABSTRACT

Enzymes with cephalosporin C acylase activity obtained by site-directed, random or "site-saturation" mutagenesis of a native sequence optimised for expression in *E. coli*.

11 Claims, 6 Drawing Sheets

FIGURE 1

```
Met Thr Met Ala Ala Asn Thr Asp Arg Ala Val Leu Gln Ala Ala Leu
1               5                   10                  15

Pro Pro Leu Ser Gly Ser Leu Pro Ile Pro Gly Leu Ser Ala Ser Val
            20                  25                  30

Arg Val Arg Arg Asp Ala Trp Gly Ile Pro His Ile Lys Ala Ser Gly
        35                  40                  45

Glu Ala Asp Ala Tyr Arg Ala Leu Gly Phe Val His Ser Gln Asp Arg
        50                  55                  60

Leu Phe Gln Met Glu Leu Thr Arg Arg Lys Ala Leu Gly Arg Ala Ala
65                  70                  75                  80

Glu Trp Leu Gly Ala Glu Ala Ala Glu Ala Asp Ile Leu Val Arg Arg
                85                  90                  95

Leu Gly Met Glu Lys Val Cys Arg Arg Asp Phe Glu Ala Leu Gly Val
                100                 105                 110

Glu Ala Lys Asp Met Leu Arg Ala Tyr Val Ala Gly Val Asn Ala Phe
            115                 120                 125

Leu Ala Ser Gly Ala Pro Leu Pro Val Glu Tyr Gly Leu Leu Gly Ala
            130                 135                 140

Glu Pro Glu Pro Trp Glu Pro Trp His Ser Ile Ala Val Met Arg Arg
145                 150                 155                 160

Leu Gly Leu Leu Met Gly Ser Val Trp Phe Lys Leu Trp Arg Met Leu
                165                 170                 175

Ala Leu Pro Val Val Gly Ala Ala Asn Ala Leu Lys Leu Arg Tyr Asp
            180                 185                 190
```

FIGURE 1

```
Asp Gly Gly Arg Asp Leu Leu Cys Ile Pro Pro Gly Ala Glu Ala Asp
        195                 200                 205

Arg Leu Glu Ala Asp Leu Ala Thr Leu Arg Pro Ala Val Asp Ala Leu
        210                 215                 220

Leu Lys Ala Met Gly Gly Asp Ala Ser Asp Ala Ala Gly Gly Gly Ser
225                 230                 235                 240

Asn Asn Trp Ala Val Ala Pro Gly Arg Thr Ala Thr Gly Arg Pro Ile
                245                 250                 255

Leu Ala Gly Asp Pro His Arg Val Phe Glu Ile Pro Gly Phe Tyr Ala
                260                 265                 270

Gln His His Leu Ala Cys Asp Arg Phe Asp Met Ile Gly Leu Thr Val
        275                 280                 285

Pro Gly Val Pro Gly Phe Pro His Phe Ala His Asn Gly Lys Val Ala
        290                 295                 300

Tyr Cys Val Thr His Ala Phe Met Asp Ile His Asp Leu Tyr Leu Glu
305                 310                 315                 320

Gln Phe Ala Gly Glu Gly Arg Thr Ala Arg Phe Gly Asn Asp Phe Glu
                325                 330                 335

Pro Val Ala Trp Ser Arg Asp Arg Ile Ala Val Arg Gly Gly Ala Asp
                340                 345                 350

Arg Glu Phe Asp Ile Val Glu Thr Arg His Gly Pro Val Ile Ala Gly
                355                 360                 365

Asp Pro Arg Asp Gly Ala Ala Leu Thr Leu Arg Ser Val Gln Phe Ala
                370                 375                 380
```

FIGURE 1

```
Glu Thr Asp Leu Ser Phe Asp Cys Leu Thr Arg Met Pro Gly Ala Ser
385             390             395             400

Thr Val Ala Gln Leu Tyr Asp Ala Thr Arg Gly Trp Gly Leu Ile Asp
            405             410             415
His Asn Leu Val Ala Gly Asp Val Ala Gly Ser Ile Gly His Leu Val
            420             425             430

Arg Ala Arg Val Pro Ser Arg Pro Arg Glu Asn Gly Trp Leu Pro Val
        435             440             445

Pro Gly Trp Ser Gly Glu His Glu Trp Arg Gly Trp Ile Pro His Glu
        450             455             460

Ala Met Pro Arg Val Ile Asp Pro Pro Gly Gly Ile Ile Val Thr Ala
465             470             475             480

Asn Asn Arg Val Val Ala Asp Asp His Pro Asp Tyr Leu Cys Thr Asp
            485             490             495

Cys His Pro Pro Tyr Arg Ala Glu Arg Ile Met Lys Arg Leu Val Ala
        500             505             510

Asn Pro Ala Phe Ala Val Asp Asp Ala Ala Ile His Ala Asp Thr
        515             520             525

Leu Ser Pro His Val Gly Leu Leu Arg Arg Arg Leu Glu Ala Leu Gly
        530             535             540

Ala Arg Asp Asp Ser Ala Ala Glu Gly Leu Arg Gln Met Leu Val Ala
545             550             555             560

Trp Asp Gly Arg Met Asp Ala Ala Ser Glu Val Ala Ser Ala Tyr Asn
            565             570             575

Ala Phe Arg Arg Ala Leu Thr Arg Leu Val Thr Asp Arg Ser Gly Leu
        580             585             590
```

FIGURE 1

| | | | | | | | | | | | |
|---|---|---|---|---|---|---|---|---|---|---|---|
|Glu|Gln|Ala|Ile|Ser|His|Pro|Phe|Ala|Val|Ala|Pro|Gly|Val|Ser|
| | |595| | | |600| | | |605| | | | |

Glu Gln Ala Ile Ser His Pro Phe Ala Val Ala Pro Gly Val Ser
            595             600              605

Pro Gln Gly Gln Val Trp Trp Ala Val Pro Thr Leu Leu Arg Asp Asp
            610             615              620

Asp Ala Gly Met Leu Lys Gly Trp Ser Trp Asp Gln Ala Leu Ser Glu
625             630              635                       640

Ala Leu Ser Val Ala Ser Gln Asn Leu Thr Gly Arg Ser Trp Gly Glu
                645             650              655

Glu His Arg Pro Arg Phe Thr His Pro Leu Ala Thr Gln Phe Pro Ala
            660             665              670

Trp Ala Gly Leu Leu Asn Pro Ala Ser Arg Pro Ile Gly Gly Asp Gly
            675             680              685

Asp Thr Val Leu Ala Asn Gly Leu Val Pro Ser Ala Gly Pro Gln Ala
            690             695              700

Thr Tyr Gly Ala Leu Ser Arg Tyr Val Phe Asp Val Gly Asn Trp Asp
705             710              715                       720

Asn Ser Arg Trp Val Val Phe His Gly Ala Ser Gly His Pro Ala Ser
            725             730              735

Ala His Tyr Ala Asp Gln Asn Ala Pro Trp Ser Asp Cys Ala Met Val
            740             745              750

Pro Met Leu Tyr Ser Trp Asp Arg Ile Ala Ala Glu Ala Val Thr Ser
            755             760              765

Gln Glu Leu Val Pro Ala Leu Glu His His His His His His
            770             775              780

FIGURE 2

```
atgactatgg cagctaatac ggatcgtgcg gttttacaag cggcgctgcc tccgttgtct    60
ggttccctgc cgattccggg cctctcggca agcgtgcggg tgcggcgtga tgcttggggt   120
atccctcata tcaaagcaag tggtgaagcg gatgcatacc gcgctcttgg cttcgttcat   180
tctcaagatc ggttgttcca aatggaactt acccggcgca aagcgctggg tcgtgctgcg   240
gagtggcttg gggcggaggc cgctgaggcg gacatcctgg tccgccgtct gggtatggaa   300
aaagtctgtc gccgcgattt cgaggctctc ggcgttgaag cgaaagatat gttacgggcc   360
tacgttgccg gggtgaatgc cttcctggca tcgggggcac ctctgcctgt ggaatacggc   420
ctgcttggtg cggaaccgga accatgggaa ccatggcaca gtatcgcggt tatgcgccgc   480
ttgggcctgc tgatggggtc tgtgtggttt aaattatggc ggatgcttgc actgccggtc   540
gtggggctg ctaacgcgtt aaaactgcgc tatgacgacg gcggcgggga tctcttgtgc   600
attccgccgg gcgccgaggc tgatcggctt gaggcggacc tcgcgacgct ccgcccagcg   660
gtcgatgcgc tgctgaaagc catgggtggg gatgctagcg acgccgctgg cggggggcagc  720
aataactggg ccgtcgctcc gggccgcacc gcaaccggtc gtccgatcct ggccggtgat   780
ccgcatcggg ttttttgagat tccgggtttt tatgctcaac atcacttagc atgtgaccgt   840
tttgatatga ttggtctgac cgtgcctggc gtcccgggct tcccacattt tgcccataac   900
ggtaaggtcg catattgtgt gacccacgca tttatggata tccacgatct ttatctggaa   960
cagttcgcag gcgaaggtcg gacggcgcgc ttcggtaacg acttcgaacc ggtggcctgg  1020
tcccgcgacc gtattgcggt tcgtggcggg gccgaccgtg aatttgatat tgtcgagacg  1080
cgtcacgggc cggttatcgc aggtgaccca cgggatggtg cagcgctgac gctgcggagc  1140
gttcagtttg cggaaacgga cctctcgttt gactgcctca ctcgcatgcc gggggccagc  1200
accgttgcgc agctgtatga tgctacccgt ggctgggggt tgattgatca caacctcgtc  1260
gccggggatg tcgcaggctc gatcgggcac cttgtgcgtg cacgggtgcc gagtcgtcca  1320
cgcgagaatg ggtggttacc ggtgcctggc tggagcggtg agcacgaatg gcggggctgg  1380
atccctcatg aagctatgcc tcgcgttatt gatcctccgg gtggtattat cgtgacggcc  1440
aacaaccggg tcgttgcgga cgaccaccct gattacttgt gcacggactg ccatccgccg  1500
taccgtgccg aacgcatcat gaaacggttg gttgcgaatc ctgcgtttgc tgtggacgat  1560
gccgccgcca tccacgcaga tactctgagt ccgcacgtcg ggctgctgcg ccgccgtctg  1620
```

FIGURE 2

```
gaagccctgg gcgcccgcga cgattcggcc gcagagggtc tccgtcagat gctggtcgcc    1680
tgggatggtc gcatggatgc agcgtccgaa gtcgcctctg cctacaatgc attccgtcgg    1740
gcgctgaccc gtctggttac tgatcggtcc gggctggaac aggctattag tcatccattt    1800
gccgcggtgg caccgggcgt ttctccacag ggccaggtgt ggtgggcggt tccgacttta    1860
ttgcgggacg atgacgctgg tatgctgaag ggttggtcct gggatcaagc attatcggaa    1920
gcgctgagcg ttgccagcca aaatctgact ggtcgctcgt ggggtgaaga acatcgtccg    1980
cgctttactc atcctctggc aactcagttt ccagcttggg caggtttgct taatccagcg    2040
agccgcccga ttggcggcga tggggatact gtcctggcga atggcctggt tccaagcgca    2100
ggccctcagg cgacgtatgg cgccttatcc cggtatgtgt tcgatgtcgg caactgggac    2160
aacagtcgtt gggtggtgtt tcatggcgca tccggtcatc cggcgagtgc gcattatgcg    2220
gaccagaatg cgccatggag tgattgtgcc atggtcccaa tgctgtattc ttgggatcgc    2280
attgcggcgg aagcggtgac ctctcaggaa ttagtcccgg ctctcgagca ccaccaccac    2340
caccactga                                                           2349
```

CEPHALOSPORIN C ACYLASES

The present invention relates to enzymes with cephalosporin C acylase activity, recombinant DNA processes for the preparation thereof, nucleotide sequences encoding for said enzymes, expression vectors containing said nucleotide sequences, cells transformed with said expression vectors and processes for the preparation of 7-amino-cephalosporanic acid by means of said enzymes.

BACKGROUND OF THE INVENTION

Cephalosporin C acylase is an enzyme that converts cephalosporin C to 7-amino-cephalosporanic acid (7-ACA), an intermediate for the preparation of a large number of semisynthetic cephalosporins.

Even if 7-ACA can be obtained from cephalosporin C by chemical synthesis, enzymatic methods are preferred in that they are more environment-friendly and less costly.

Conventional enzymatic procedures for the conversion of cephalosporin C in 7-ACA require two different enzymes, a D-amino acid oxidase (DAAO) and a glutaryl acylase. DAAO transforms cephalosporin C into α-Keto-adipoyl-7ACA with concomitant production of hydrogen peroxide. α-Keto-adipoyl-7ACA is then oxidized to glutaryl-7-ACA with hydrogen peroxide (produced by oxidative deamination and/or added to the reaction medium), thereafter glutaryl acylase hydrolyses glutaryl-7-ACA to 7-ACA. The conventional process requires two separate enzymatic reactors, and the presence or addition of hydrogen peroxide can inactivate the immobilized enzymes, which impairs the plant and increases costs.

Attempts have been made to develop enzymes able to directly hydrolyse cephalosporin C to 7-ACA. Three known enzymes, referred to as SE83, N176 and V22, isolated from *Pseudomonas* strains, possess this ability (Journal of Fermentation and Bioengineering Vol. 72(4), 232-243, 1991), but their acylase activity is higher on glutaryl-7ACA than on cephalosporin C.

Mutants and recombinant DNA methods for their preparation have been disclosed (U.S. Pat. No. 5,320,948, EP 475652, EP 558241, U.S. Pat. No. 5,804,429) to improve the characteristics of these enzymes, in particular specificity, stability and activity.

However, there is still the need for enzymes with improved cephalosporin C acylase activity, in terms of kinetics, stability, activity and specificity and which can be expressed in high amounts.

DISCLOSURE OF THE INVENTION

A gene encoding an enzyme with cephalosporin acylase activity has been designed based on the sequence of a known acylase from *Pseudomonas* N176 (Aramori I. et al. (1991). *Cloning and Nucleotide Sequencing of New Glutaryl 7-ACA and Cephalosporin C Acylase Genes from Pseudomonas Strains Journal of Fermentation and Bioengineering*; 72(4), 232-243). It is reported that this acylase is active both on glutaryl-7ACA and—although to a lower extent—on cephalosporin C.

When designing the starting gene (named wild-type HisVAC) various variations were inserted:
- introduction of a phenylalanine at the 270 position; this mutation (known from the literature) increases the activity on cephalosporin C (Ishii Y. et al. (1995) *High-level production, chemical modification and site-directed mutagenesis of a cephalosporin C acylase from Pseudomonas strain N176 Eur. J. Biochem;* 230, 773-778).
- introduction of an additional sequence (consisting of amino acids LEHHHHHH [SEQ ID NO: 3]) at the C-terminus, so as not to interfere with the active site region (the first amino acid of the β subunit is involved in the catalysis). Said sequence was introduced in order to make the subsequent chromatographic purification easier, using pET24 plasmid as the cloning and expression vector. This plasmid is resistant to kanamycin and is able to insert a "His-Tag sequence" at the C-terminus of the protein and a "T7-Tag sequence" at the N-terminus. Regions containing the restriction sites for EcoRI, XhoI and NdeI were added at the gene ends by means of the polylinker of pET24, so as to facilitate cloning into the plasmid.
- removal of some restriction sites in the gene (BamHI and NheI) by replacement of some bases, so as not to introduce undesired alterations in the corresponding aminoacid sequence, i.e. using the *E. coli's* codon usage.
- optimisation of the nucleotide sequence to *E. coli* codon usage, using the most translated codons (in particular, the sequence encoding for the N-terminal position of the protein was significantly modified), the main mutations being:

1. substitution of the GGA codon for glycine, scarcely used in *E. coli*;
2. substitution of the AGG and CGA codons for arginine, scarcely used in *E. coli*;
3. substitution of the ATA codon for isoleucine, scarcely used in *E. coli*;
4. substitution of the CCC codon for proline, scarcely used in *E. coli*;
5. balance in the use of the GAG and GAA codons for glutamic acid, according to their frequency in *E. coli*;
6. balance in the use of TTT and TTC codons for phenylalanine, according to their frequency in *E. coli*;
7. balance in the use of the CAG and CAA codons for glutamine, according to their frequency in *E. coli*;
8. balance in the use of the CAT and CAC codons for histidine, according to their frequency in *E. coli*.

The resulting cDNA has a sequence identity of 63.7% with the native N176 gene.

HisVAC-encoding cDNA was then obtained by chemical synthesis (Itakura K, Rossi J J, Wallace R B Synthesis and use of synthetic oligonucleotides. Annu Rev Biochem. 1984; 53:323-56).

It has now been found that some specific mutations allow to remarkably improve the properties of the "wild-type" enzyme (hereinafter referred to as HisVAC).

Figure 1:
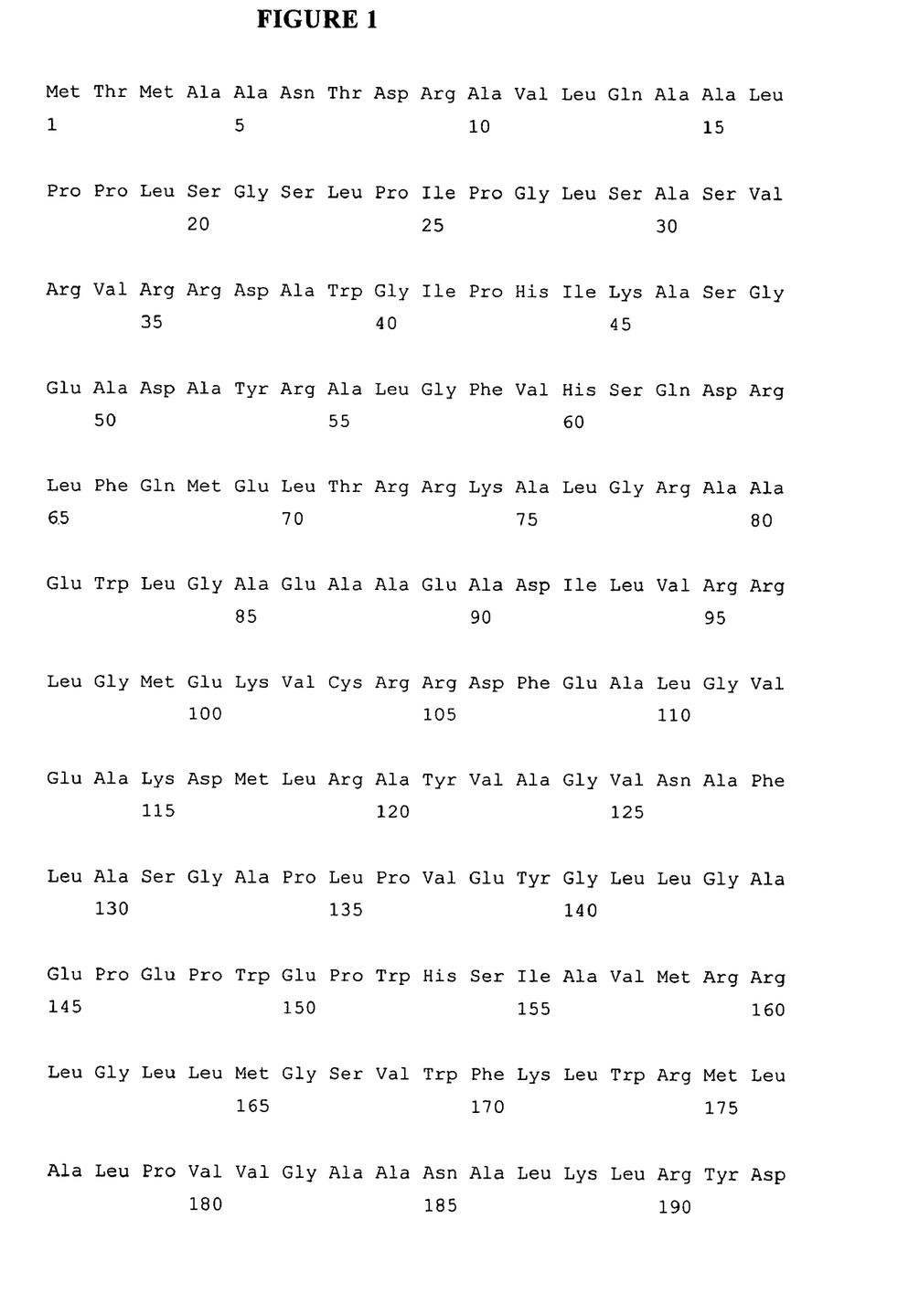
FIG. 1: SEQ ID NO:1—HisVAC amino acid sequence.

In particular, the invention provides enzymes with cephalosporin C acylase activity having the amino acid sequence reported in FIG. 1 (SEQ. ID No. 1), wherein one or more of the following mutations have been inserted:

replacement of alanine 215 with Tyr, Phe, Glu or Val;
replacement of histidine 296 with Asn, Ser, Thr, Phe;
replacement of aspartic acid 416 and histidine 417 with any other amino acids;
replacement of the amino acids at the 261, 271, 294, 297, 307, 308 and 309 positions with any other amino acids.

Particularly preferred are the enzymes wherein:
alanine 215 is replaced with Tyr;
alanine 215 is replaced with Phe;
alanine 215 is replaced with Glu;
alanine 215 is replaced with Val;
histidine 296 is replaced with Asn;
histidine 296 is replaced with Ser;
histidine 296 is replaced with Thr;
histidine 296 is replaced with Phe;
alanine 215 is replaced with Tyr and histidine 296 is replaced with Ser.

Arginine 263 of the "wild-type" enzyme must not be replaced.

Figure 2:
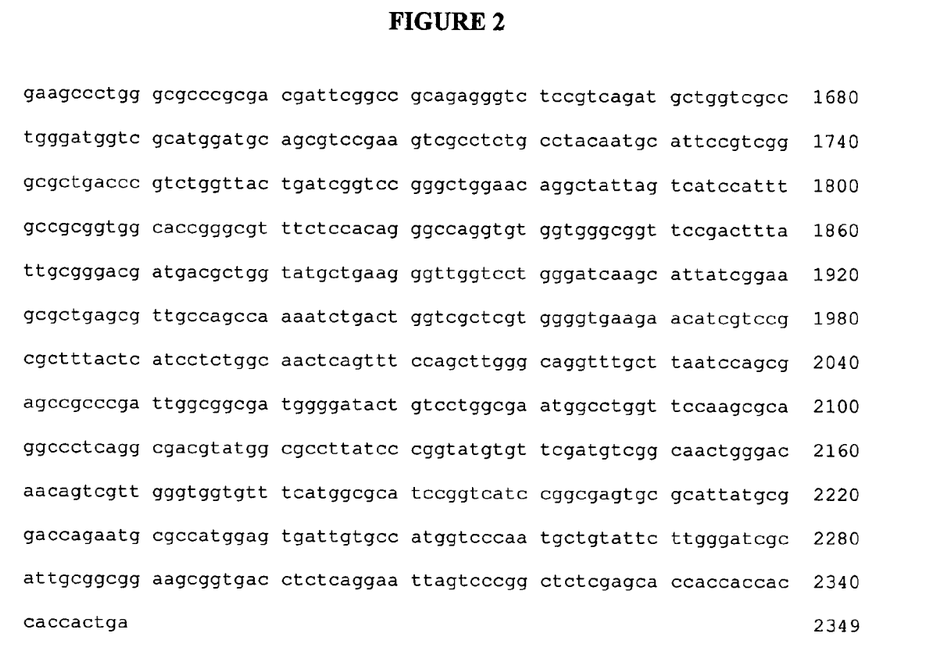
FIG. 2: SEQ ID NO:2—Wild-type HisVAC-encoding cDNA.

The enzymes of the invention can be prepared with a process comprising:

insertion of a DNA sequence obtainable by site-direct mutagenesis, random or exhaustive mutagenesis of the nucleotide sequence reported in FIG. 2 (SEQ. ID No. 2) into an expression vector for bacteria or eukariotic cells;
transformation of bacterial or eukariotic cells with said vectors;
culture of the transformed cells, extraction and recovery of the expression product.

The mutated sequences of the invention can then be inserted in plasmid expression vectors with conventional methods, which can be used to transform E. coil competent cells able to produce the enzymes.

For the envisaged industrial uses, the enzymes can be linked to a solid carrier, such as a synthetic polymer insoluble in the aqueous medium used in the enzymatic conversion of cephalosporin C to 7-amino-cephalosporanic acid. Suitable resins for immobilization of the acylase are those with an acrylic type structure, with epoxy functional groups, such as Sepabeads EC-EP (Resindion srl—Mitsubishi Chemical Corporation) and Eupergit C (Rohm-Degussa), or with primary amino groups, such as Sepabeads EC-has and EC-EA (Resindion srl—Mitsubishi Chemical Corporation). In any case, the enzyme is brought in contact with the resin and immobilized through the high reactivity of the functional groups (epoxides) or activation of the resin with a bifunctional agent, such as glutaraldehyde, so as to bind the enzyme to the matrix. Other resins suitable for acylase immobilization are polystyrene resins, macroreticular resins and resins with basic functional groups, such as Sepabeads EC-Q1A: the enzyme is absorbed on the resin and then stabilized by crosslinking with a bifunctional agent (glutaraldehyde).

EXAMPLES

Example 1

Microorganisms Culture and Fermentation

E. coli strains containing the expression plasmid for HisVAC are maintained culturing single colonies isolated from agar plates. All the strains show a satisfactory growth rate in different agar media, in particular LB and LB Miller media (with and without 1% glucose), having a pH of 7.0 and the following composition:

LB=tryptone (pancreatic casein digest) 10 g/l; yeast extract 5 g/l; NaCl 5 g/l;
LB Miller=tryptone (pancreatic casein digest) 10 g/l; yeast extract 5 g/l; NaCl 10 g/l.

The agar plates are incubated at 37° C. for 1 day, thereafter the cells are scraped off. The colonies remain viable keeping the plates at 4° C. for several weeks.

The cells are suspended in a sterile solution and the suspension (grown to $OD_{600}$=4) is trasferred into a flask (or a fermenter, after completion of the vegetative phase in flask) with LB Miller medium containing 34 gg/ml chloramphenicol and 30 µg/ml kanamycin. The culture is grown at 37° C., 200 rpm for 3 hours to $OD_{600}$=0.8 (exponential phase). After the productive phase, induction is carried out by addition of 0.6 mM IPTG, then the cells are grown at 21 or 25° C. for 3-5 hours.

Extraction and Purification of Wild-type HisVAC Acylase

HisVAC is an endocellular acylase; after fermentation the culture broth is centrifuged and lysis of the cell membrane is accomplished by chemical (addition of detergents or sodium hydroxide for few seconds) or physical (press or glass beads mill) treatments. The preferred method is resuspension of the cell paste in a buffer solution, such as phosphate or pyrophosphate buffer (pH 7.5-8) followed by lysis with French Press o Rannie Homogenizer, at 600-800 bar. The cell lysate is clarified by centrifugation or microfiltration (cut-off 0.45 µm), optionally in the presence of polyelectrolytes. The clarified solution containing the crude enzyme is purified by chromatography. The preferred procedure is the purification through a column containing a chelating resin with iminodiacetic groups that bind metal ions (for example zinc or nickel), able to selectively absorb histidine-tagged proteins. Suitable chromatographic resins are HiTrap Chelating (Amersham Biosciences) and Sepabeads FP-IDA (Resindion srl—Mitsubishi Chemical Corporation). Highly pure HisVAC acylase can be obtained by elution with increasing imidazole concentrations or pH changes.

Purified HisVAC is stable after 120 min incubation at pH ranging from 5 to 9. Enzymatic activity increases as a function of the pH of the reaction solution, in the range 5-10, reaching the highest value at 40° C. after 30 minutes reaction.

Production of HisVAC Acylase by Means of a Culture of Escherichia coli BL21(DE3)pLysS Transformed with pET24Δ-HisVAC Plasmid 1) Microorganism Preparation HisVAC-encoding cDNA (wild-type and mutants, 2322 bp) is digested with NdeI and BamHI restriction enzymes. This cDNA is ligated to the 3.6 kb fragment corresponding to the NdeI-BamHI-digested pET24Δ(Bg1II-Tth111I)-HisVAC expression plasmid. This plasmid was obtained by cleavage of the 7.6 kb pET24-HisVAC plasmid (obtained by cloning of the whole VAC cDNA treated with XhoI/NdeI restriction enzyme (2.3 kb) into the 5.3 kb fragment of the pET24 plasmid digested with XhoI/NdeI) by means of BgIII and Tth111I restriction enzymes, recovery of the 4984 bp fragment, blunting of the cohesive ends by means of Klenow enzyme and ligation. The resulting pETA-HisVAC is used to transform BL21(DE3)pLysS *E. coli* cells. The transformed cells are transferred to an LB-agar plate containing 34 µg/ml chloramphenicol and 30 µg/ml kanamycin, and incubated at 37° C. for 24 hours. Single colonies are selected from the plate and cultured in 750 ml of liquid LB Miller medium containing 34 µg/ml chloramphenicol and 30 µg/ml kanamycin. The presence of pET24Δ-HisVAC plasmid in the cells is checked by restriction analysis of the recovered plasmid DNA.

2) Fermentation a) Productive Phase

BL21(DE3)pLysS *E. coli* cells transformed with pET24Δ-HisVAC plasmid are fermented at 37° C. for 24 hours in solid LB-agar medium containing 34 µg/ml chloramphenicol and 30 µg/ml kanamycin. The cells are resuspended in 100 ml of sterile solution and 15 ml of the suspension (grown to $OD_{600}=4$) is transferred into a 2 l flask (or into a fermenter following the growth in a flask until completion of the vegetative phase) containing 750 ml of LB Miller medium with 34 µg/ml chloramphenicol and 30 µg/ml kanamycin. The culture is grown at 37° C., 200 rpm for 3 hours to $OD_{600}=0.8$ (exponential phase).

b) Induction Phase

After the productive phase, induction is accomplished by addition of 0.6 mM IPTG. After induction the cells are grown at 21 or 25° C.; the highest enzyme production is reached after 3-5 hours.

Example 2

Extraction and Purification of Wild-type HisVAC Acylase

Cell paste (13 g, corresponding to 90 U of HisVAC acylase) obtained from 4.5 litres of broth as described in Example 1 is resuspended in 39 ml of 50 mM buffer phosphate, pH 7.5 with 0.7 µg/ml pepstatin. The suspension is cooled to 4° C. and passed through a French Press. The lysate is clarified by centrifugation at 39000 g for 60 minutes. 50 ml of clarified solution with HisVAC acylase activity of 1.8 U/ml, corresponding to 90 total units, is obtained. This crude sample is loaded onto a 5 ml HiTrap Chelating column (Amersham Biosciences), previously loaded with nickel ions and equilibrated with 50 mM sodium pyrophosphate buffer, 1 M NaCl and 20 mM imidazole buffer, pH 7.2. HisVAC acylase is eluted with 6 ml of 50 mM sodium pyrophosphate buffer, 500 mM imidazole, 10% glycerol, pH 7.2. The purified enzyme has an activity of 12 U/ml (72 total units) and a specific activity of 6.5 U/mg proteins, with glutaryl-7ACA as the substrate.

Example 3

Immobilization of HisVAC Acylase on EC-EP Sepabeads 1 g of EC-EP Sepabeads is added to 10 ml of 1 M potassium phosphate buffer, pH 8.0 at 20° C., containing 100 acylase units. The mixture is left under mild stirring for 12 hours at 20° C., then allowed to stand for further 12 hours at 20° C. The resin is recovered by filtration and washed with 25 mM potassium phosphate buffer, pH 8.0. The resulting biocatalyst has an immobilized activity of 35-40 U/g with glutaryl-7ACA as the substrate.

Example 4

Conversion of Cephalosporin C with HisVAC Acylase in Solution 0.053 g cephalosporin C, dihydrate sodium salt (86% purity) is dissolved in 20 ml of 100 mM potassium phosphate buffer, pH 8 (2.27 g/l, assuming a 100% purity) and added to 6.4 ml purified acylase (167.2 total units). The mixture is incubated at 20° C., under stirring, keeping the pH at 8 by addition of diluted sodium hydroxide. The maximum conversion to 7-ACA is achieved after 150 minutes (92.8% conversion, HPLC).

Example 5

Mutants Preparation

1. Site-directed Mutagenesis

Nucleotide mutations are introduced using a "QuikChange® Site-Directed Mutagenesis Kit" (STRATAGENE) that allows to introduce mutations in specific sites of double stranded DNA. Double stranded pET24Δ-HisVAC containing the gene of interest and two primers with the desired mutations are also used. The primers, each complementary to the corresponding vector strand, are elongated using PfuTurbo® DNA polymerase which replicates both plasmid strands with high fidelity. After the PCR, the mixture is treated with Dpn I (an endonuclease specific for methylated DNA that is used to digest parental DNA) and the product is used to transform XLI-Blue supercompetent cells, from which DNA is extracted to transform the *E. coli* expression strain BL21(DE3)pLysS.

About 50 ng of template DNA (pET24Δ-HisVAC); 125 ng of each primer; 2.5 U PfuTurbo® DNA polymerase are used, running the following PCR program:

```
95° C. for 30"
95° C. for 30"  ⎤
57° C. for 1'    ⎥ 14 cycles
68° C. for 12'  ⎦
4° C. ∞
```

The mutated proteins obtained by site-directed mutagenesis were purified as described in example 2.

2. Site-saturation Mutagenesis

To obtain libraries of random recombinant HisVAC mutants, site-saturation (or exhaustive) mutagenesis is used, as it allows to insert any one of the 20 amino acids in the same position of the protein. This technique consists in the use of degenerated oligonucleotides to introduce different mutations in a specific target codon. The oligonucleotides are synthesized using an equimolar nucleoside mixture (dA, dC, dG, dT) in correspondence of the position to be "saturated". The resulting mutant gene population consists of identical genes having a random codon. In the different clones this codon can codify for any amino acid and therefore a library of mutants with all possible amino acid substitutions at one specific target residue is obtained. pET24Δ-AcyHis expression plasmid was used as the DNA template and oligonucleotides degenerated in all the three bases of the codon encoding the specific residue (e.g. the amino acids at positions 215 and 296) were used as the primers.

Mutations were introduced using a "QuikChange Site-Directed Mutagenesis Kit" (STRATAGENE), also used for site-specific mutagenesis. Mutated DNA is used to transform the expression strain BL21(DE3)pLysS. Mutated clones were then subjected to screening and purified as described in example 2.

3. Random Mutagenesis

Libraries of recombinant HisVAC enzyme mutants were prepared by amplification of the gene of interest through error-prone PCR. Amplification was carried out under different mutagenesis conditions:
  a. 10% DMSO, 1 mM 2-mercaptoethanol and high cycles number;
  b. $[Mn^{++}]$=0.5 mM, $[Mg^{++}]$=0.25 mM, [dGTP] and [dATP]= 0.2 mM, [dCTP] and [dTTP]=1 mM.

pET24Δ-AcyHis expression plasmid (see below) was used as the DNA template and two designed oligonucleotides, RND-ACY-EXT (5'-CGAGATCTCGATCCCGCGAAA-3' [SEQ ID NO:4]) and RND-ACY-UP (5'-AACCAAC-CGTTTCATGATGCTTCGGC-3'[SEQ ID NO:5]), were used as the primers. These primers anneal to vector regions flanking the sites for NdeI and BamHI restriction enzymes, as shown in the following scheme:

In order to isolate the amplificated band (~1.6 kb) from the DNA template (7.6 kb), PCR products are pooled and separated on agarose gel. Amplified DNA is then gel-purified and subjected to preparative digestion with NdeI and BamHI restriction enzymes. The digestion mixture is loaded on agarose gel and the fragment of interest (~1.4 kb) is recovered and gel purified. The extracted DNA was subjected to O.N. digestion with NdeI and BamHI restriction enzymes; two fragments of 3.6 kb and 1.4 kb were obtained. The fragment of interest (3.6 kb) was recovered and gel-purified. DNA encoding for AcyHis enzyme, amplificated under mutagenesis conditions, digested and purified, is ligated to the expression vector pET24Δ(BglII-Tth111)-AcyHis. The ligation mixture is used to transform E. coli strain JM109.

In order to transfer the "mutants library" in E. coli BL21 (DE3)pLysS (expression strain), the cells are transformed with the pool of plasmid DNA which contains all the obtained mutants. For this purpose all the colonies obtained by transformation of the JM109 cells with the ligation product are resuspended in selective medium and total plasmid DNA is extracted. This DNA is used to transform BL21(DE3)pLysS expression strain.

Example 6

Characterization of the Mutants Obtained by Mutagenesis

Kinetics parameters of the mutants and HisVAC acylase were determined measuring the hydrolysis of cephalosporin C or glutaryl 7-ACA in 0.1 M phosphate buffer solution, pH 8.0 at 37° C. (then converted in units at 25° C.). The amount of 7-ACA is determined spectrophotometrically, using a standard curve, measuring the yellow intensity at 415 nm (Schiff base), resulting upon reaction with p-dimethylaminobenzaldehyde, using modified Bulasingham method (Biochem. Biophys. Acta 276, 250, 1972).

One acylase unit is the amount of enzyme (in solution or immobilized) which, under the assay conditions, produces one micromole of 7-ACA/minute.

According to the data reported in the following tables, the mutants of the invention have better kinetic properties on cephalosporin C than on glutaryl-7-ACA compared with wild-type HisVAC acylase.

|  | Gl-7-ACA | | | | | | Cef C | | | | | |
| --- | --- | --- | --- | --- | --- | --- | --- | --- | --- | --- | --- | --- |
|  | wild-type | A215E | A215F | A215L | A215V | A215Y | wild-type | A215E | A215F | A215L | A215V | A215Y |
| Vmax (U/mg) | 24.2 | 2 | 3.3 | 6.2 | 12.5 | 16 | 0.23 | 0.16 | 0.21 | 0.75 | 0.78 | 1.8 |
| Km (mM) | 1.6 | 1 | 0.85 | 1.7 | 1.2 | 1.7 | 8.2 | 3.2 | 7.7 | 9.5 | 8.3 | 6.9 |
| Vmax/Km | 15.5 | 2.1 | 3.9 | 3.7 | 10.1 | 9.4 | 0.03 | 0.05 | 0.03 | 0.08 | 0.09 | 0.26 |
| Inhibition after | 12.5 mM | 25 mM | 50 mM | 12.5 mM | 12.5 mM | 12.5 mM | 50 mM | NO inhibit. | NO inhibit. | 12.5 mM | 50 mM | 25 mM |

Moreover, mutant A215Y is more stable at temperatures higher than 25° C.

|  | Gl-7-ACA | | | | Cef C | | | | |
| --- | --- | --- | --- | --- | --- | --- | --- | --- | --- |
|  | wild-type | H296N | H296S | H296T | H296F | wild-type | H296N | H296S | H296T | H296F |
| Vmax (U/mg) | 24.2 | 4.3 | 2.0 | 0.67 | 1.7 | 0.23 | 0.27 | 0.63 | 0.2 | 0.05 |
| Km (mM) | 1.6 | 2.8 | 0.7 | 2.0 | 1.9 | 8.2 | 5.2 | 7.7 | 4.8 | 4.1 |
| Vmax/Km | 15.5 | 1.5 | 2.8 | 0.33 | 0.9 | 0.03 | 0.05 | 0.08 | 0.04 | 0.01 |
| Inhibition after | 12.5 mM | 50 mM | 25 mM | 50 mM | 50 mM | 50 mM | 50 mM | 25 mM | 60 mM | 60 mM |

|  | Gl-7-ACA | | | | Cef C | | | |
| --- | --- | --- | --- | --- | --- | --- | --- | --- |
|  | wild-type | H417Y | D416Y | D416Y–H417Y | wild-type | H417Y | D416Y | D416Y–H417Y |
| Vmax (U/mg) | 24.2 | 14.8 | 4.9 | 1.2 | 0.23 | 0.05 | 0.66 | 4.2 |
| Km (mM) | 1.6 | 4.3 | 1.75 | 9 | 8.2 | 12.3 | 7.2 | 13.1 |
| Vmax/Km | 15.5 | 3.4 | 2.8 | 0.13 | 0.03 | 0.004 | 0.09 | 0.3 |
| Inhibition after | 12.5 mM | NO inhibit. | 25 mM | 12.5 mM | 50 mM | 50 mM | NO inhibit. | 50 mM |

|  | G1-7-ACA | | Cef C | |
| --- | --- | --- | --- | --- |
|  | Wild-type | A215Y-H296S | Wild-type | A215Y-H296S |
| Vmax (U/mg) | 24.2 | 2.2 | 0.23 | 0.66 |
| Km (mM) | 1.6 | 4 | 8.2 | 10 |
| Vmax/Km | 15.5 | 0.55 | 0.03 | 0.07 |
| Inhibition after | 12.5 mM | 25 mM | 50 mM | 40 mM |

Product-inhibition data are reported in the following table. The data show significant changes in product inhibition of mutated acylases with respect to wild-type HisVAC.

|  | $K_i$ (mM) | | |
| --- | --- | --- | --- |
|  | G1-7-ACA | | Cef C |
|  | 7-ACA | Glutaric Acid | α-Aminoadipic |
| Wild-type | 0.1 mM | 13.6 mM | 67.7 mM |
| A215Y | 11.3 mM | 6.1 mM | no inhibition |
| A215F | 4.7 mM | 2.1 mM | 85.2 mM |

The invention claimed is:

1. A cephalosporin C acylase having the amino acid sequence set forth in SEQ ID NO:1 comprising an amino acid mutation at one or more of positions 215, 261, and 294, wherein the alanine at position 215 is replaced with an amino acid selected from the group consisting of tyrosine, phenylalanine, glutamate, and valine; or the amino acids at positions 261 and 294 are replaced with any other amino acid.

2. The cephalosporin C acylase of claim 1, wherein the alanine at position 215 is replaced with tyrosine.

3. The cephalosporin C acylase of claim 1, wherein the alanine at position 215 is replaced with phenylalanine.

4. The cephalosporin C acylase of claim 1, wherein the alanine at position 215 is replaced with glutamate.

5. The cephalosporin C acylase of claim 1, wherein the alanine at position 215 is replaced with valine.

6. The cephalosporin C acylase of claim 1, further comprising replacing the histidine at position 296 with asparagine.

7. The cephalosporin C acylase of claim 1, further comprising replacing the histidine at position 296 with serine.

8. The cephalosporin C acylase of claim 1, further comprising replacing the histidine at position 296 with threonine.

9. The cephalosporin C acylase of claim 1, further comprising replacing the histidine at position 296 with phenylalanine.

10. The cephalosporin C acylase of claim 7, wherein the alanine at position 215 is replaced with tyrosine and the histidine at position 296 is replaced with serine.

11. A process for the preparation of cephalosporins which comprises hydrolysis and acylation of cephalosporin C with the cephalosporin C acylase of claim 1 in the presence of a suitable acylating agent.

\* \* \* \* \*

SEQUENCE LISTING

<160> NUMBER OF SEQ ID NOS: 5

<210> SEQ ID NO 1
<211> LENGTH: 782
<212> TYPE: PRT
<213> ORGANISM: Pseudomonas

<400> SEQUENCE: 1

```
Met Thr Met Ala Ala Asn Thr Asp Arg Ala Val Leu Gln Ala Ala Leu
 1               5                   10                  15

Pro Pro Leu Ser Gly Ser Leu Pro Ile Pro Gly Leu Ser Ala Ser Val
                20                  25                  30

Arg Val Arg Arg Asp Ala Trp Gly Ile Pro His Ile Lys Ala Ser Gly
            35                  40                  45

Glu Ala Asp Ala Tyr Arg Ala Leu Gly Phe Val His Ser Gln Asp Arg
        50                  55                  60

Leu Phe Gln Met Glu Leu Thr Arg Arg Lys Ala Leu Gly Arg Ala Ala
```

```
                65                  70                  75                  80
Glu Trp Leu Gly Ala Glu Ala Glu Ala Asp Ile Leu Val Arg Arg
                    85                  90                  95
Leu Gly Met Glu Lys Val Cys Arg Arg Asp Phe Glu Ala Leu Gly Val
                100                 105                 110
Glu Ala Lys Asp Met Leu Arg Ala Tyr Val Ala Gly Val Asn Ala Phe
                115                 120                 125
Leu Ala Ser Gly Ala Pro Leu Pro Val Glu Tyr Gly Leu Leu Gly Ala
                130                 135                 140
Glu Pro Glu Pro Trp Glu Pro Trp His Ser Ile Ala Val Met Arg Arg
145                 150                 155                 160
Leu Gly Leu Leu Met Gly Ser Val Trp Phe Lys Leu Trp Arg Met Leu
                165                 170                 175
Ala Leu Pro Val Val Gly Ala Ala Asn Ala Leu Lys Leu Arg Tyr Asp
                180                 185                 190
Asp Gly Gly Arg Asp Leu Leu Cys Ile Pro Pro Gly Ala Glu Ala Asp
                195                 200                 205
Arg Leu Glu Ala Asp Leu Ala Thr Leu Arg Pro Ala Val Asp Ala Leu
                210                 215                 220
Leu Lys Ala Met Gly Gly Asp Ala Ser Asp Ala Ala Gly Gly Gly Ser
225                 230                 235                 240
Asn Asn Trp Ala Val Ala Pro Gly Arg Thr Ala Thr Gly Arg Pro Ile
                245                 250                 255
Leu Ala Gly Asp Pro His Arg Val Phe Glu Ile Pro Gly Phe Tyr Ala
                260                 265                 270
Gln His His Leu Ala Cys Asp Arg Phe Asp Met Ile Gly Leu Thr Val
                275                 280                 285
Pro Gly Val Pro Gly Phe Pro His Phe Ala His Asn Gly Lys Val Ala
                290                 295                 300
Tyr Cys Val Thr His Ala Phe Met Asp Ile His Asp Leu Tyr Leu Glu
305                 310                 315                 320
Gln Phe Ala Gly Glu Gly Arg Thr Ala Arg Phe Gly Asn Asp Phe Glu
                325                 330                 335
Pro Val Ala Trp Ser Arg Asp Arg Ile Ala Val Arg Gly Gly Ala Asp
                340                 345                 350
Arg Glu Phe Asp Ile Val Glu Thr Arg His Gly Pro Val Ile Ala Gly
                355                 360                 365
Asp Pro Arg Asp Gly Ala Ala Leu Thr Leu Arg Ser Val Gln Phe Ala
                370                 375                 380
Glu Thr Asp Leu Ser Phe Asp Cys Leu Thr Arg Met Pro Gly Ala Ser
385                 390                 395                 400
Thr Val Ala Gln Leu Tyr Asp Ala Thr Arg Gly Trp Gly Leu Ile Asp
                405                 410                 415
His Asn Leu Val Ala Gly Asp Val Ala Gly Ser Ile Gly His Leu Val
                420                 425                 430
Arg Ala Arg Val Pro Ser Arg Pro Arg Glu Asn Gly Trp Leu Pro Val
                435                 440                 445
Pro Gly Trp Ser Gly Glu His Glu Trp Arg Gly Trp Ile Pro His Glu
                450                 455                 460
Ala Met Pro Arg Val Ile Asp Pro Pro Gly Gly Ile Ile Val Thr Ala
465                 470                 475                 480
Asn Asn Arg Val Val Ala Asp Asp His Pro Asp Tyr Leu Cys Thr Asp
                485                 490                 495
```

```
Cys His Pro Pro Tyr Arg Ala Glu Arg Ile Met Lys Arg Leu Val Ala
            500                 505                 510

Asn Pro Ala Phe Ala Val Asp Asp Ala Ala Ile His Ala Asp Thr
        515                 520                 525

Leu Ser Pro His Val Gly Leu Leu Arg Arg Arg Leu Glu Ala Leu Gly
        530                 535                 540

Ala Arg Asp Asp Ser Ala Ala Glu Gly Leu Arg Gln Met Leu Val Ala
545                 550                 555                 560

Trp Asp Gly Arg Met Asp Ala Ala Ser Glu Val Ala Ser Ala Tyr Asn
                565                 570                 575

Ala Phe Arg Arg Ala Leu Thr Arg Leu Val Thr Asp Arg Ser Gly Leu
                580                 585                 590

Glu Gln Ala Ile Ser His Pro Phe Ala Val Ala Pro Gly Val Ser
        595                 600                 605

Pro Gln Gly Gln Val Trp Trp Ala Val Pro Thr Leu Leu Arg Asp Asp
    610                 615                 620

Asp Ala Gly Met Leu Lys Gly Trp Ser Trp Asp Gln Ala Leu Ser Glu
625                 630                 635                 640

Ala Leu Ser Val Ala Ser Gln Asn Leu Thr Gly Arg Ser Trp Gly Glu
                645                 650                 655

Glu His Arg Pro Arg Phe Thr His Pro Leu Ala Thr Gln Phe Pro Ala
            660                 665                 670

Trp Ala Gly Leu Leu Asn Pro Ala Ser Arg Pro Ile Gly Gly Asp Gly
                675                 680                 685

Asp Thr Val Leu Ala Asn Gly Leu Val Pro Ser Ala Gly Pro Gln Ala
    690                 695                 700

Thr Tyr Gly Ala Leu Ser Arg Tyr Val Phe Asp Val Gly Asn Trp Asp
705                 710                 715                 720

Asn Ser Arg Trp Val Val Phe His Gly Ala Ser Gly His Pro Ala Ser
                725                 730                 735

Ala His Tyr Ala Asp Gln Asn Ala Pro Trp Ser Asp Cys Ala Met Val
            740                 745                 750

Pro Met Leu Tyr Ser Trp Asp Arg Ile Ala Ala Glu Ala Val Thr Ser
        755                 760                 765

Gln Glu Leu Val Pro Ala Leu Glu His His His His His
    770                 775                 780

<210> SEQ ID NO 2
<211> LENGTH: 2349
<212> TYPE: DNA
<213> ORGANISM: Pseudomonas

<400> SEQUENCE: 2
atgactatgg cagctaatac ggatcgtgcg gttttacaag cggcgctgcc tccgttgtct      60
ggttccctgc cgattccggg cctctcggca agcgtgcggg tgcggcgtga tgcttggggt     120
atccctcata tcaaagcaag tggtgaagcg gatgcatacc gcgctcttgg cttcgttcat     180
tctcaagatc ggttgttcca atggaacttt acccggcgca aagcgctggg tcgtgctgcg     240
gagtggcttg gggcggaggc cgctgaggcg gacatcctgg tccgccgtct gggtatggaa     300
aaagtctgtc gccgcgattt cgaggctctc ggcgttgaag cgaaagatat gttacgggcc     360
tacgttgccg gggtgaatgc cttcctggca tcggggcac ctctgcctgt ggaatacggc     420
ctgcttggtg cggaaccgga accatgggaa ccatggcaca gtatcgcggt tatgcgccgc     480
```

```
ttgggcctgc tgatgggggtc tgtgtggttt aaattatggc ggatgcttgc actgccggtc    540
gtgggggctg ctaacgcgtt aaaactgcgc tatgacgacg gcgggcggga tctcttgtgc    600
attccgccgg gcgccgaggc tgatcggctt gaggcggacc tcgcgacgct ccgcccagcg    660
gtcgatgcgc tgctgaaagc catgggtggg gatgctagcg acgccgctgg cggggggcagc    720
aataactggg ccgtcgctcc gggccgcacc gcaaccggtc gtccgatcct ggccggtgat    780
ccgcatcggg ttttttgagat tccgggtttt tatgctcaac atcacttagc atgtgaccgt    840
tttgatatga ttggtctgac cgtgcctggc gtcccgggct tcccacattt tgcccataac    900
ggtaaggtcg catattgtgt gacccacgca tttatggata tccacgatct ttatctggaa    960
cagttcgcag gcgaaggtcg gacggcgcgc ttcggtaacg acttcgaacc ggtggcctgg   1020
tcccgcgacc gtattgcggt tcgtggcggg gccgaccgtg aatttgatat tgtcgagacg   1080
cgtcacgggc cggttatcgc aggtgaccca cgggatggtg cagcgctgac gctgcggagc   1140
gttcagtttg cggaaacgga cctctcgttt gactgcctca ctcgcatgcc ggggggccagc   1200
accgttgcgc agctgtatga tgctacccgt ggctgggggt tgattgatca aacctcgtc    1260
gccggggatg tcgcaggctc gatcgggcac cttgtgcgtg cacgggtgcc gagtcgtcca   1320
cgcgagaatg ggtggttacc ggtgcctggc tggagcggtg agcacgaatg gcggggctgg   1380
atccctcatg aagctatgcc tcgcgttatt gatcctccgg gtggtattat cgtgacggcc   1440
aacaaccggg tcgttgcgga cgaccaccct gattacttgt gcacggactg ccatccgccg   1500
taccgtgccg aacgcatcat gaaacggttg gttgcgaatc ctgcgtttgc tgtggacgat   1560
gccgccgcca tccacgcaga tactctgagt ccgcacgtcg ggctgctgcg ccgccgtctg   1620
gaagccctgg gcgccgcgcga cgattcggcc gcagagggtc tccgtcagat gctggtcgcc   1680
tgggatggtc gcatggatgc agcgtccgaa gtcgcctctg cctacaatgc attccgtcgg   1740
gcgctgaccc gtctggttac tgatcggtcc gggctggaac aggctattag tcatccatttt   1800
gccgcggtgg caccgggcgt ttctccacag ggccaggtgt ggtgggcggt tccgactttta   1860
ttgcgggacg atgacgctgg tatgctgaag ggttggtcct gggatcaagc attatcggaa   1920
gcgctgagcg ttgccagcca aaatctgact ggtcgctcgt ggggtgaaga acatcgtccg   1980
cgctttactc atcctctggc aactcagttt ccagcttggg caggtttgct taatccagcg   2040
agccgcccga ttggcggcga tggggatact gtcctggcga atggcctggt tccaagcgca   2100
ggccctcagg cgacgtatgg cgccttatcc cggtatgtgt tcgatgtcgg caactgggac   2160
aacagtcgtt gggtggtgtt tcatggcgca tccggtcatc cggcgagtgc gcattatgcg   2220
gaccagaatg cgccatggag tgattgtgcc atggtcccaa tgctgtattc ttgggatcgc   2280
attgcggcg aagcggtgac ctctcaggaa ttagtcccgg ctctcgagca ccaccaccac   2340
caccactga                                                          2349
```

<210> SEQ ID NO 3
<211> LENGTH: 8
<212> TYPE: PRT
<213> ORGANISM: Artificial sequence
<220> FEATURE:
<223> OTHER INFORMATION: polypeptide added to C-terminus to aid in
      purification of pET24 plasmid

<400> SEQUENCE: 3

Leu Glu His His His His His His
1               5

```
<210> SEQ ID NO 4
<211> LENGTH: 21
<212> TYPE: DNA
<213> ORGANISM: Artificial sequence
<220> FEATURE:
<223> OTHER INFORMATION: oligonucleotide primer with homology to pET24
      expression plasmid

<400> SEQUENCE: 4
cgagatctcg atcccgcgaa a                                                  21

<210> SEQ ID NO 5
<211> LENGTH: 26
<212> TYPE: DNA
<213> ORGANISM: Pseudomonas

<400> SEQUENCE: 5
aaccaaccgt ttcatgatgc ttcggc                                             26
```